(12) United States Patent
Samuels

(10) Patent No.: US 9,840,734 B2
(45) Date of Patent: *Dec. 12, 2017

(54) METHODS FOR ANALYZING DNA

(71) Applicant: Raindance Technologies, Inc., Lexington, MA (US)

(72) Inventor: Michael Samuels, Windham, NH (US)

(73) Assignee: Raindance Technologies, Inc., Billerica, MA (US)

( * ) Notice: Subject to any disclaimer, the term of this patent is extended or adjusted under 35 U.S.C. 154(b) by 238 days.

This patent is subject to a terminal disclaimer.

(21) Appl. No.: 14/058,799

(22) Filed: Oct. 21, 2013

(65) Prior Publication Data

US 2014/0113300 A1    Apr. 24, 2014

Related U.S. Application Data

(60) Provisional application No. 61/716,992, filed on Oct. 22, 2012.

(51) Int. Cl.
*C12Q 1/68*    (2006.01)

(52) U.S. Cl.
CPC .................................. *C12Q 1/686* (2013.01)

(58) Field of Classification Search
None
See application file for complete search history.

(56) References Cited

U.S. PATENT DOCUMENTS

| 5,527,670 | A | * | 6/1996 | Stanley | C12N 15/10 |
| | | | | | 435/6.12 |
| 5,700,637 | A | * | 12/1997 | Southern | 435/6.12 |
| 5,985,567 | A | * | 11/1999 | Rampal | 435/6.12 |
| 2015/0247191 | A1 | * | 9/2015 | Zhang | B01L 3/5027 |
| | | | | | 506/2 |

OTHER PUBLICATIONS

Nakano et al., "Single-molecule PCR using water-in-oil emulsion," Journal of Biotechnology, 2003, vol. 102, pp. 117-124.*

* cited by examiner

*Primary Examiner* — Young J Kim
(74) *Attorney, Agent, or Firm* — Brown Rudnick LLP; Thomas C. Meyers

(57) ABSTRACT

The invention generally relates to methods for increasing the amount of DNA available for analysis when using partitioned samples and parallel processing. For example, double-stranded DNA can be dissociated into two single-stranded components, and the single strands partitioned into different droplets prior to analysis. The disclosed methods are useful for performing digital PCR analysis on samples where the target DNA is not in abundance, for example when the sample originates from a body fluid or an FFPE sample.

11 Claims, 5 Drawing Sheets

METHODS FOR ANALYZING DNA

CROSS-REFERENCE TO RELATED APPLICATIONS

This application claims priority to, and the benefit of, U.S. Provisional Application 61/716,992, filed Oct. 22, 2012, the contents of which are incorporated herein by reference in its entirety.

FIELD OF THE INVENTION

The invention relates to methods for analyzing DNA in samples, in particular samples having small amounts of detectable DNA, such as fine needle aspirates, blood plasma, forensic samples, or FFPE samples.

BACKGROUND

Several breakthrough medical assays depend on an ability to quantify amounts of DNA in a sample. For example, copy number variation assays can be used to type cancers. For a patient identified as having lung cancer, a copy number variation assay can determine whether the patient has non-small-cell cancer by measuring the number of extra copies of epidermal growth factor receptor (EGFR) genes present is a sample from a patient. Based up the copy number variation results, a prognosis can be made quicker and suitable treatment can be started. Other medical assays, such as gene expression assays, use quantitative DNA detection to assess the progression of a disease. For example, a blood sample may be assayed for absolute amounts of DNA corresponding to biomarkers indicative of a disease, e.g., cystic fibrosis. The quantity of biomarkers from an identified panel can give information about the stage of the disease or whether treatments are improving the disease.

DNA quantification is also useful for evaluating the DNA from a sample prior to performing expensive analytical assays such as sequencing. For example, formalin-fixed, paraffin-embedded (FFPE) tissue specimens, which have been stored at room temperature for years can provide a wealth of genetic material for various molecular biology studies, such as expression profiling and sequence analysis. However, the DNA in some FFPE tissue samples degrades extensively during the storage, while the DNA in other samples is mostly intact. The amount of degradation can severely diminish the value of sequencing results. The ability to know prior to sequencing (or PCR) how much valuable DNA is present avoids wasting resources on samples without recoverable DNA. Pre-sequencing evaluation of the quantity of DNA present is also helpful in forensic science, where a blood stain, etc., may not have valuable DNA present.

Improved methods for quantifying DNA are available. In particular, real-time PCR has greatly improved the analysis of DNA from both throughput and quantitative perspectives. While traditional PCR typically relies on end-point, and sometimes semi-quantitative, analysis of amplified DNA targets via agarose gel electrophoresis, real-time PCR (or qPCR) is geared toward accurately quantifying exponential amplification as the PCR reaction progresses. Typically, qPCR reactions are monitored either using a variety of highly sequence-specific fluorescent probe technologies, or by using non-specific DNA intercalating fluorogenic dyes.

Stochastic sampling of PCR results in counting errors, especially when the starting material has little DNA, or when the sample containing the DNA targeted for counting also has large amounts of background DNA. Stochastic errors arise when random fluctuations are amplified, as is the case when a DNA sample is amplified during or before counting. In some instances, a target DNA will be missed in the first round of amplification leading to a final DNA count smaller than it should be. In other instances, a non-target DNA will be mistakenly amplified in the first round (or subsequent rounds) of amplification leading to a final DNA count higher than it should be. Thus, the resulting biased post-amplification DNA count does not represent the true condition of the sample from which it was obtained. Such errors have real consequences when the counting assay is relied upon for directing treatment for a disease.

Digital PCR (dPCR) is an alternative quantitation method in which dilute samples are divided into many separate reactions. See for example, Brown et al. (U.S. Pat. Nos. 6,143,496 and 6,391,559) and Vogelstein et al. (U.S. Pat. Nos. 6,440,706, 6,753,147, and 7,824,889), the content of each of which is incorporated by reference herein in its entirety. Typically, dPCR is conducted in a "terminal dilution" regime wherein there are at least two containers for each target molecule, however in practice there are typically more than two containers for each target molecule. At terminal dilution, the vast majority of reactions contain either one or zero target DNA molecules. The principle advantage of digital compared to qPCR is that it avoids any need to interpret the time dependence of fluorescence intensity—an analog signal—while avoiding the uncertainty of non-exponential amplification during early PCR cycles. That is, PCR amplifying a partitioned sample in the terminal dilution regime should be "all or nothing;" either a target DNA was in the partitioned sample or not. Additionally, it is more reliable to assess a "yes/no" answer with respect to a fluorescent event, as opposed to correlating a fluorescence intensity with a number of fluorescent moieties.

Nonetheless, digital PCR methods are still subject to stochastic sampling errors during sample partitioning. That is, some partitioned samples will contain more than one target DNA molecule, skewing counting methods based upon the digital readout. See, Fu et al., "Counting Individual DNA Molecules by the Stochastic Attachment of Diverse Labels," *PNAS,* 108(22), 9026-9031 (2011), incorporated by reference herein in its entirety. In the terminal dilution regime, this error is negligible when there is sufficient target DNA to achieve a meaningful number of counts. When there is little target DNA in the original sample, however, the stochastic errors become meaningful, and the resultant DNA counts must be reported with much larger errors. See Fu et al.

SUMMARY

When assaying samples with less than optimum amounts of target DNA, the invention can be used to effectively double the number of target molecules in a sample available for analysis, thereby reducing the errors associated with the small sample size. Such samples may be, for example, blood serum (cell-free DNA samples), fine needle aspirates, or samples recovered from FFPE tissues. However, the method is generally applicable to any DNA sample. The methods generally involve dissociating a target double-stranded DNA (dsDNA) sequence into its component strands, i.e., single-stranded DNA (ssDNA), and then separately partitioning each strand prior to amplification and counting.

Using the methods of the invention, DNA assays that partition DNA from a sample and then analyze the partitioned portions in parallel, e.g., using multi-well plates or droplet processing, will be improved. The invention allows the number of targets per sample to be doubled, while not providing additional DNA. In some instances, the improvement in target number in a sample will allow a sample to be assayed for a disease when that sample would have been rejected using conventional techniques, i.e., partitioning the double-stranded DNA from the sample. For example, using conventional techniques, a DNA assay may be meaningless because the signal (e.g., DNA counts) is similar in size to the random errors present in the assay. However, using the methods of the invention, the DNA count signal can be doubled, making it discernible from the noise, and giving meaning to the assay.

In one instance, the invention is a method for detecting DNA in a sample. The method includes dissociating a double-stranded DNA from a sample into a first strand and a second strand, partitioning the first strand and the second strand into different partitioned portions, and detecting the presence of the first strand or the second strand in a partitioned portion. In some embodiments, the detection is done by performing a PCR reaction in the partitioned portion, thereby changing a fluorescent property of the partitioned portion, for example, because a fluorescent label is incorporated into an amplicon during the PCR reaction. After the PCR reaction is complete, the fluorescent property of the partitioned portion can be analyzed to determine the presence of DNA in the sample. The disclosed methods for detecting DNA in a sample can be used to evaluate the quantity and quality of DNA that is obtained from a biological sample, e.g., a blood sample. The invention allows the DNA to be evaluated for quantity and quality, e.g., number of relevant sequences, prior to amplification and/or sequencing. Thus, using the methods of the invention, it is possible to avoid performing expensive measurements (e.g., sequencing) on a sample that does not contain sufficient DNA.

In another instance, the invention is a method for determining an amount of DNA in a sample. The method includes dissociating a plurality of double-stranded DNAs from a sample into a plurality of first strands and a plurality of second strands, partitioning the plurality of first strands and the plurality of second strands into a plurality of partitioned portions (at least some of the partitioned portions having only a first strand or only a second strand), detecting the presence or absence of a first strand or a second strand in a plurality of partitioned portions, and comparing the presence of a first strand or a second strand in a plurality of partitioned portions to the absence of a first strand or a second strand in a plurality of partitioned portions to determine an amount of DNA present in a sample. In some embodiments, detecting the presence or absence of a first strand or a second strand is done by performing a PCR reaction in at least some of the partitioned portions, thereby changing a fluorescent property in at least some of the partitioned portions, for example, because a fluorescent label is incorporated into an amplicon in at least some of the partitioned portions during the PCR reaction. After the PCR reaction is complete, the fluorescent property of the partitioned portions can be analyzed to determine the presence or absence of DNA in a partitioned portion, thereby allowing the determination of an amount of DNA in the sample.

The disclosed methods can be expanded and used to determine the progression of a disease in a subject. Such a method includes obtaining a biological sample comprising a plurality of double-stranded DNAs from a subject, dissociating the plurality of double-stranded DNAs into a plurality of first strands and a plurality of second strands, partitioning the plurality of first strands and the plurality of second strands into a plurality of partitioned portions, at least some of the partitioned portions having only a first strand or only a second strand, detecting the presence or absence of a targeted sequence in the plurality of partitioned portions, and determining the number of occurrences of the targeted sequence, wherein the number of occurrence of the targeted sequence is indicative of a progression of a disease. Again, detecting the presence or absence of a targeted sequence may be done by performing a PCR reaction in at least some of the partitioned portions, thereby changing a fluorescent property in at least some of the partitioned portions, for example, because a fluorescent label is incorporated into an amplicon in at least some of the partitioned portions during the PCR reaction.

The invention includes various methods for dissociating double-stranded DNA and subsequently partitioning the single strands prior to amplification and reacting with hybridization probes, for example. In one embodiment, the dsDNA is incubated at an elevated temperature, e.g., 90° C. or greater, for a time sufficient to dissociate the two strands. In an embodiment, the ssDNAs are subsequently rapidly cooled to prevent reannealing. In some embodiments, the rapid cooling is done prior to partitioning. In other embodiments, the ssDNAs can be prevented from reannealing by adding a chemical species, e.g., a salt, or by adding single-stranded DNA-binding protein to maintain the ssDNA in solution. In other embodiments, the ssDNAs can be prevented from reannealing by limiting their diffusion by dilution or addition of a chemical reagent.

In one embodiment, the dissociating methods are used to form droplets containing single-stranded DNA. One method involves heating a sample fluid comprising a plurality of double stranded DNAs to at least about 90° C., thereby dissociating the double stranded DNAs into single-stranded DNA and contacting the sample fluid with reagents for conducting amplification and generation of specific fluorescent signals (e.g. PCR primers, probes, polymerase, dNTPs, buffer) prior to introduction into separate compartments (e.g. microfluidic droplets). In another embodiment, the dissociated ssDNA molecules are contacted with a carrier fluid in a microfluidic channel to thereby form droplets containing single-stranded DNA.

In another embodiment, the ssDNA is used to create a first fluid comprising the ssDNA. The first fluid is then partitioned into a large number of reactors. In an embodiment, each reactor is a droplet. In an embodiment, most of the reactors will be populated with only one ssDNA or with no ssDNA. In one embodiment, the first fluid comprises reagents for conducting amplification and generation of specific fluorescent signals (e.g. PCR primers, probes, polymerase, dNTPs, buffers). In another embodiment, the first fluid does not comprise reagents for conducting amplification and generation of specific fluorescent signals, and a second fluid is added (either continuous, or discontinuous as in droplets), containing the reagents for conducting amplification and generation of specific fluorescent signals. Using massive parallel qPCR amplification, the single stranded DNA in each reactor is amplified and allowed to bind to or incorporate probes. Each reactor is then analyzed for the presence of the probe or a change in probe properties. The probe analysis provides information about the number of target DNAs present in the original sample. This information can then be used to evaluate the progression of a disease in a patient, for example.

BRIEF DESCRIPTION OF DRAWINGS

FIG. 3A depicts the droplet generation chip; FIG. 3B depicts the droplet spacing for readout; and FIG. 3C depicts a cartoon of droplet readout by fluorescence.

FIG. 4A shows droplet fluorescence during readout for the most concentrated sample. Each discrete burst of fluorescence corresponded to an individual droplet. Two different groups of droplets were evident: PCR(+) droplets peaking at ~0.8 V and PCR(−) droplets at ~0.1 V; FIG. 4B shows a histogram of the peak fluorescence intensities of droplets from the complete data trace in (a). PCR(+) and PCR(−) droplets appeared as two very distinct populations centered at 0.78 and 0.10 V, respectively; FIG. 4C shows the serial dilution of template DNA. Open circles: measured occupancies; solid line: the best fit to Eqn 2 (A=0.15, f=4.8, $R^2$−0.9999).

FIG. 5A depicts a template DNA that is amplified with a forward primer (F1) and a reverse primer (R1). FIG. 5B depicts droplets containing the target sequence emit fluorescence and are detected by laser. FIG. 5C depicts fluorescence detected by a laser. The number of microcapsules either containing or not containing the target sequence is shown in a histogram (FIG. 5D) and quantified (FIG. 5E).

DETAILED DESCRIPTION

Figure 1:
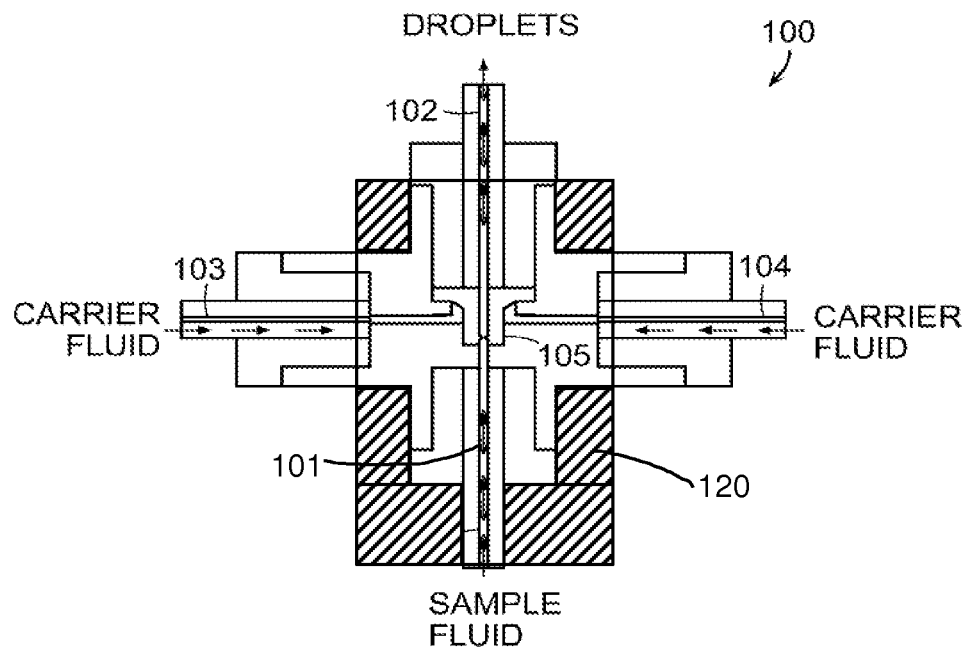
FIG. 1 depicts a droplet formation device.

The invention provides a method for increasing the number of DNA samples that can be partitioned into separate reactors (e.g., containers or droplets) when using sample partition methods for DNA counting, such as digital PCR, e.g. digital droplet PCR. Using the methods of the invention, the number of DNA samples that are available for counting can be effectively doubled. In the case of a sample that has only small amounts of target DNA, doubling the sample size can dramatically reduce the error rates in the final count. Thus, the disclosed methods are most valuable when performing DNA counting assays (e.g., copy number variation, genetic profiling) on samples with less than optimum levels of target DNA. Such conditions are commonly found when assaying samples obtained with less-invasive techniques, such as blood, aspirates, urine, or sputum. Low target DNA levels are also common in FFPE samples and forensic samples, which may have been improperly collected or stored for long periods of time.

The invention broadly applies to digital nucleic acid detection techniques and, in specific embodiments, digital PCR in droplets. Using such techniques, a DNA sample is typically digested or fragmented, and then partitioned into a number of reactors, each reactor having a single segment of double-stranded DNA. Each dsDNA can then be amplified, labeled, and detected, as required by the goals of the assay. As an improvement to the known techniques, the disclosed methods allow the DNA sample to be partitioned into reactors such that each reactor contains a target molecule, e.g., a single-stranded DNA target. As a result of this improvement, it is possible to double the amount of PCR positive droplets (i.e., double the amplicon yield) without the need for more DNA. As such, errors due to stochastic sampling of a sample, especially a sample having only a small amount of DNA, are reduced.

The invention includes various methods that can be used for dissociating double-stranded DNA and subsequently stabilizing the single strands for partitioning and reacting with hybridization probes, for example. In one embodiment, the dsDNA is incubated at an elevated temperature, e.g., 90° C. or greater, for a time to dissociate the two strands. In an embodiment, the ssDNAs are subsequently rapidly cooled to prevent reannealing prior to partitioning. In other embodiments, the ssDNAs can be prevented from reannealing by adding a chemical species, e.g., a salt, or by adding single-stranded DNA-binding protein to maintain the ssDNA in solution. In other embodiments, the ssDNAs can be prevented from reannealing by limiting their diffusion by dilution or addition of a chemical reagent.

In one embodiment, a first fluid comprising the ssDNA is contacted with a second fluid containing reagents for conducting amplification and generation of specific fluorescent signals (e.g. PCR primers, probes, polymerase, dNTPs, buffer) prior to introduction into separate compartments (e.g. microfluidic droplets). Typically, most of the reactors will be populated with only one ssDNA or with no ssDNA.

In another embodiment the dissociated ssDNA molecules are first partitioned into a large number of reactors, e.g., droplets. To the reactors, e.g., droplets, a second fluid is added (either continuous, or discontinuous as in droplets). The second fluid contains one or more primer pairs, and one or more probes specific for the target DNA. The second fluid may also contain reagents for conducting a PCR reaction, such as a polymerase and dNTPs. Using massive parallel qPCR amplification, the single stranded DNA in each reactor is amplified and allowed to bind to or incorporate probes. Each reactor is then analyzed for the presence of the probe or a change in probe properties. The probe analysis provides information about the number of target DNAs present in the original sample. This information can then be used to evaluate the progression of a disease in a patient, for example.

The second fluid includes probes, which typically include a detectable label. The second fluid may have multiple labels, for example multiple copies of the same detectable label, or different detectable labels. The detectable labels may be fluorescent labels, or the labels may be moieties that will bind to fluorescent labels. The labels may also be sequences that are unique and identifiable with sequencing. The plurality of probes can include one or more groups of probes at varying concentrations. The one or more groups of probes can include the same detectable label which varies in intensity upon detection, due to the varying probe concentrations.

The first and second fluids can each be in droplet form. Any technique known in the art for forming droplets may be used with methods of the invention. An exemplary method involves flowing a stream of the sample fluid containing the ssDNAs such that it intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets containing the first fluid. An exemplary sample fluid is an aqueous fluid and an exemplary carrier fluid is oil. In certain embodiments, the carrier fluid includes a surfactant, such as a fluorosurfactant. The same method may be applied to create individual droplets from the second fluid containing the primer pairs (and, in some implementations, the amplification reagents). Either the droplets containing the first fluid, the droplets containing the second fluid, or both, may be formed and then stored in a library for later merging, aspects of certain implementations of which are described in U.S. patent application Ser. No. 12/504,764, hereby incorporated herein by reference in its entirety.

Once formed, droplets containing the first and second fluids can be merged to form single droplets containing a single ssDNA template and heterogeneous mixture of primer pairs and probes. Merging can be accomplished, for example, in the presence of an electric field. Moreover, it is not required that both fluids be in the form of droplets when merging takes places. One exemplary method for merging of fluid portions with droplets is taught, for example, in U.S. patent application Ser. No. 12/729,462, hereby incorporated herein by reference in its entirety.

In an embodiment, the ssDNA is amplified in the droplets. Any method known in the art may be used to amplify the target nucleic acids either linearly or exponentially. A preferred method is the polymerase chain reaction (PCR). For purposes of the invention, other amplification techniques commonly known in the art, such as rolling circle amplification, isothermal amplification, or any combination of amplification methods using loci specific primers, nested-primers, or random primers (such primers, and/or primers used for PCR, are included in the term "amplification reagents"), may be used. In one embodiment, the ssDNA template in each of the merged/formed droplets is amplified by thermocycling the droplets under temperatures/conditions sufficient to conduct a PCR reaction.

The resulting amplicons in the droplets can then be analyzed. For example, the presence or absence of the ssDNA in one or more droplets can be detected optically, e.g., by the detectable label on the plurality of probes. In another embodiment, the amplicons may be sequenced.

In certain embodiments, analyzing the droplets involves determining a number of droplets that contain a target ssDNA and a number of droplets that contain no ssDNA. In these embodiments, the mere presence of the target ssDNA is indicative of a disease. For example, the ssDNA may be pathogenic ssDNA, e.g., originating from a bacterium. Determining an amount of ssDNA present in the sample will provide information about the severity of the pathogenic infection. The presence of specific ssDNA may also be indicative of a stage of disease, e.g., pathogenic infection.

In another embodiment, analysis will involve determining a number of a first ssDNA and a number of a second ssDNA. In these embodiments the relative amount of first ssDNA is indicative of the presence of, or the progression of, a disease. The number of second ssDNAs may be used to normalize the measured level of first ssDNA. The second ssDNA may be a sequence that is highly conserved in the species from which the sample was obtained, and the amount of the second ssDNA may be unlikely to vary substantially between subjects of the species. In other embodiments, a plurality of ssDNAs may be analyzed and normalized in order to measure an expression level of a gene profile.

Generally, the presence of a greater number of target ssDNAs than expected is indicative of a disease, such as cancer. In other embodiments, e.g., in which a disease is associated with the downregulation of a gene, the absence of an expected number of target ssDNAs is indicative of a disease, such as cancer. The methods may also be used to determine the severity of a disease, or a response to drug therapy.

In another embodiment, the methods can be used for detecting a recurrence of a cancer in a patient. Those methods may involve forming sample droplets containing a single target ssDNA derived from a patient sample, flowing the sample droplets through a channel, amplifying the ssDNA in the droplets, detecting the amplified target in the droplets, and analyzing the droplets to determine the presence of an amount of target ssDNA. In certain embodiments, the analyzing step includes capturing amplicons obtained from the droplets using labeled capture probes. The sample may be a human tissue or body fluid. Exemplary body fluids are pus, sputum, semen, urine, blood, saliva, stool, and cerebrospinal fluid. In other aspects of the invention generally provide a method for forensic identification of low levels of target nucleic acid in an environment having multiple other sources of nucleic acid, e.g., DNA. Such methods may also be practiced using fluids compartmentalized in containers other than or in addition to droplets.

Methods in accordance with the invention also encompass the use of a primer. The methods include providing a fluid comprising the sample ssDNA and a primer, wherein the primer has at least one unique related probe and is selected to be complementary to a targeted sequence. The method also includes partitioning the fluid into a plurality of partitions, wherein at least a first portion of the partitions comprise one molecule of ssDNA having sequence(s) complementary to the primer, and at least one related probe, and a second portion of the partitions comprising no molecules of ssDNA having sequence(s) complementary to the primer. The method further includes conducting a PCR reaction in the partitioned portions, thereby changing a fluorescent property of the first portion of the partitions, detecting the fluorescent property of each partition, and determining the number of occurrences in the sample nucleic acid of one or targeted sequences based on the detecting step. In some aspects of the invention, the method further includes comparing a first number of occurrences of a first targeted sequence to a second number of occurrences of a second targeted sequence.

Additional embodiments of the invention contemplate the use of a primer as well as rely on something other than a probe for detecting the amplified sequence. In certain embodiments, the method comprises dissociating dsDNA in a sample and partitioning the sample comprising ssDNA into a plurality of partitioned portions, wherein each portion comprises, on average a single ssDNA molecule. The method further includes introducing at least two primers, in which each primer is specific for a first or a second location on the ssDNA, the first and second locations being spaced apart from each other. The method further includes amplifying the nucleic acid in the partitioned portions, detecting the amplicons in the partitioned portions, and determining a nucleic acid make-up of the sample based on the results of the detecting step.

Methods in accordance with the invention also encompass the analysis of cell-free DNA in a biological sample. Collecting and assaying cell-free DNA provides advantages over analysis of cellular DNA in that anomalies, e.g., mutations, are easier to identify in the absence of massive quantities of normal DNA. For example, circulating cell-free tumor DNA has been detected in the serum, plasma, and blood of cancer patients. Cell-free DNA is versatile in that it can be analyzed to detect the presence of mutations, or epigenetic markers of a disease. Cell-free DNA can also be used to identify the presence of foreign pathogens, e.g., a bacterial infection. In some embodiments, the biological sample can be blood, saliva, sputum, urine, semen, transvaginal fluid, cerebrospinal fluid, sweat, breast milk, breast fluid (e.g., breast nipple aspirate), stool, a cell or a tissue biopsy.

In some instances cell-free DNA is greatly degraded, for example, because the DNA was partially digested by normal metabolic processes in the body. The invention allows the cell-free DNA to be evaluated for quality, e.g., continuity, prior to amplification and sequencing. Thus, a cell-free DNA sample can be partitioned into samples comprising ssDNA of different lengths, primers can be introduced along with appropriate probes, the ssDNA amplified, and the make-up, e.g., the continuity of the cell-free DNA sample can be determined.

dsDNA Dissociation and ssDNA Stabilization

A number of methods may be used to dissociate dsDNA into its component single strands. Typically, the goal of the dissociation process is to disrupt the hydrogen bonds between the paired complimentary bases on each of the strands, thereby allowing the two strands to separate. For example, an aqueous solution comprising dsDNA may be dissociated by heating the solution. Typically, it is necessary to heat the aqueous solution comprising dsDNA to at least about 75° C., e.g., at least about 80° C., e.g., at least about 85° C., e.g., at least about 90° C., e.g., at least about 95° C., to dissociate the two strands. Typically, an aqueous solution comprising dsDNA is maintained at an elevated temperature for at least 10 seconds or longer, e.g., at least 20 seconds or longer, e.g., at least 30 seconds or longer, e.g., at least 1 minute or longer, e.g., at least 5 minutes or longer, in order to achieve 90% or greater dissociation of the dsDNA. In other embodiments, the hydrogen bonding between the complimentary base pairs can be disrupted by changing the ionic strength of the solution, for example, by adding acids, bases, or salts to the aqueous solution comprising dsDNA. In another embodiment enzymes, such as helicases, can be used to dissociate the dsDNA into the ssDNA components.

In one embodiment, the ssDNAs are partitioned into a plurality of reactors, e.g., for digital PCR, while the conditions of the solution are more favorable to ssDNA than dsDNA. For example, a solution containing dsDNA may be raised to 90° C. or greater, allowing the dsDNA to dissociate into ssDNA, and then the solution containing ssDNA partitioned into a plurality of reactors, e.g., droplets. In an embodiment, the ssDNA can be partitioned such that each reactor contains only one, or no, ssDNA.

In other embodiments, the ssDNA may be thermally- or chemically-stabilized prior to partitioning. For example, a solution containing dsDNA may be raised to 90° C. or greater, allowing the dsDNA to dissociate into ssDNA, and then the solution containing ssDNA rapidly (snap) cooled to less than 20° C., e.g., less than 15° C., e.g., less than 10° C. The reduction in temperature is typically achieved very quickly, e.g., in two minutes or less, e.g., in one minute or less, e.g., in 45 seconds or less, e.g., in 30 seconds or less, e.g., in 20 seconds or less. At these lower temperatures, the ssDNAs are unlikely to reanneal, because the dynamic motion of the ssDNAs has been greatly reduced, making it difficult for two ssDNAs to arrange themselves for complimentary annealing. Rapid cooling may be achieved with various techniques, including ice baths, cold fingers, Peltier (thermoelectric) cooling, or liquid nitrogen. The solution containing ssDNA can then be partitioned at this lower temperature.

After partitioning, the reactors are typically returned to a condition that is favorable for the formation of dsDNA. For example, the reactors may be heated (or cooled) to 37° C. Returning the ssDNA to normal physiologic conditions will be necessary when PCR amplification in used in subsequent assay steps. That is, during the PCR process, an environment conducive to ssDNA-nucleic acid binding must be provided so that template DNA's can anneal with primers and dNTPs. In embodiments where the dsDNA is disrupted by modifying the chemical environment of the dsDNA prior to partitioning, it will be necessary to return the partitioned portion to physiologic conditions prior to performing additional assay steps, e.g., PCR.

Digital PCR

Ideally, the sensitivity of digital PCR is limited only by the number of independent amplifications that can be analyzed, which has motivated the development of several ultra-high throughput miniaturized methods allowing millions of single molecule PCR reactions to be performed in parallel (discussed in detail elsewhere). In a preferred embodiment of the invention, digital PCR is performed in aqueous droplets separated by oil using a microfluidics system. In another preferred embodiment, the oil is a fluorinated oil such as the FLUORINERT oils (3M). In a still more preferred embodiment the fluorinated oil contains a surfactant, such as PFPE-PEG-PFPE triblock copolymer, to stabilize the droplets against coalescence during the amplification step or at any point where they contact each other. Microfluidic approaches allow the rapid generation of large numbers (e.g., $10^6$ or greater) of very uniformly sized droplets that function as picoliter volume reactors (see reviews of droplet-based microfluidics). The invention is not limited to dPCR performed in water-in-oil emulsions, but rather is general to all methods of reaction compartmentalization for dPCR. In much of the Detailed Description, the invention is described in terms of the use of droplets for reactors, but it is understood that this choice of description is not limiting for the invention, and that all of the methods of the invention are compatible with other methods for partitioning a sample for parallel processing, e.g., well-plates.

Nucleic Acid Target Molecules

Nucleic acid molecules include deoxyribonucleic acid (DNA) and/or ribonucleic acid (RNA). Nucleic acid molecules can be synthetic or derived from naturally occurring sources. The invention is primarily concerned with DNA because it naturally exists as two strands that can be separated under the proper conditions. In one embodiment, DNA is isolated from a biological sample containing a variety of other components, such as proteins, lipids and non-template nucleic acids. DNA can be obtained from any cellular material, obtained from an animal, plant, bacterium, fungus, or any other cellular organism. In certain embodiments, the DNA is obtained from a single cell. Biological samples for use in the present invention include viral particles or preparations. DNA can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for DNA for use in the invention. DNA can also be isolated from cultured cells, such as a primary cell culture or a cell line. The cells or tissues from which DNA is obtained can be infected with a virus or other intracellular pathogen. In certain embodiments, the DNA binds or is allowed to bind to other target molecules such as proteins, enzymes, substrates, antibodies, binding agents, beads, small molecules, peptides, or any other molecule and serve as a surrogate for quantifying and/or detecting the target molecule. Generally, DNA can be extracted from a biological sample by a variety of techniques such as those described by Maniatis, et al., *Molecular Cloning: A Laboratory Manual*, Cold Spring Harbor, N.Y., pp. 280-281 (1982).

Droplet Formation

Methods of the invention involve forming sample droplets where some droplets contain zero target ssDNA, some droplets contain one target ssDNA, and some droplets may or may not contain multiple ssDNAs (corresponding to limiting or terminal dilution, respectively, as defined above). In the preferred embodiment, the distribution of ssDNAs within droplets obeys the Poisson distribution. However, methods for non-Poisson loading of droplets are known to those familiar with the art, and include but are not limited to active sorting of droplets, such as by laser-induced fluorescence, or by passive one-to-one loading. The description that follows assumes Poisson loading of droplets, but such description is not intended to exclude non-Poisson loading, as the invention is compatible with all distributions of DNA loading that conform to limiting or terminal dilution.

The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41,780) and European publication number EP2047910 to Raindance Technologies Inc. The content of each of which is incorporated by reference herein in its entirety.

Figure 2:
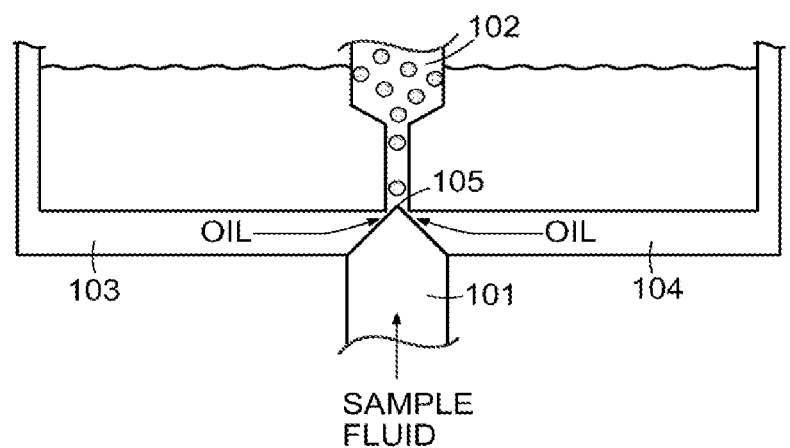
FIG. 2 depicts a portion of the droplet formation device of FIG. 1.

FIG. 1 shows an exemplary embodiment of a device 100 for droplet formation. Device 100 includes an inlet channel 101, an outlet channel 102, and two carrier fluid channels 103 and 104. Device 100 may additionally comprise a temperature block 120 to control the temperature of the fluids during droplet formation. Temperature block 120 may be used to heat or cool the fluids as needed, and may be connected to a temperature controller (not shown) to control the temperature during droplet formation. Channels 101, 102, 103, and 104 meet at a junction 105. Inlet channel 101 flows sample fluid to the junction 105. Carrier fluid channels 103 and 104 flow a carrier fluid that is immiscible with the sample fluid to the junction 105. Inlet channel 101 narrows at its distal portion wherein it connects to junction 105 (see FIG. 2). Inlet channel 101 is oriented to be perpendicular to carrier fluid channels 103 and 104. Droplets are formed as sample fluid flows from inlet channel 101 to junction 105, where the sample fluid interacts with flowing carrier fluid provided to the junction 105 by carrier fluid channels 103 and 104. Outlet channel 102 receives the droplets of sample fluid surrounded by carrier fluid.

The sample fluid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with nucleic acid molecules can be used. The carrier fluid is one that is immiscible with the sample fluid. The carrier fluid can be a non-polar solvent, decane (e.g., tetradecane or hexadecane), fluorocarbon oil, silicone oil or another oil (for example, mineral oil).

In certain embodiments, the carrier fluid contains one or more additives, such as agents which increase, reduce, or otherwise create non-Newtonian surface tensions (surfactants) and/or stabilize droplets against spontaneous coalescence on contact. Surfactants can include Tween, Span, fluorosurfactants, and other agents that are soluble in oil relative to water. In some applications, performance is improved by adding a second surfactant, or other agent, such as a polymer or other additive, to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be coated with a surfactant or a mixture of surfactants. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

In certain embodiments, the carrier fluid may be caused to flow through the outlet channel so that the surfactant in the carrier fluid coats the channel walls. In one embodiment, the fluorosurfactant can be prepared by reacting the perflourinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., FLUO-RINERT (3M)), which then serves as the carrier fluid.

One approach to merging sample fluids, using a device called a lambda injector, involves forming a droplet, and contacting the droplet with a fluid stream, in which a portion of the fluid stream integrates with the droplet to form a mixed droplet. In this approach, only one phase needs to reach a merge area in a form of a droplet. Further description of such method is shown in pending U.S. patent application Ser. No. 13/371,222, the content of which is incorporated y reference herein in its entirety.

According to a method for operating the lambda injector, a droplet is formed as described above. After formation of the sample droplet from the first sample fluid, the droplet is contacted with a flow of a second sample fluid stream. Contact between the droplet and the fluid stream results in a portion of the fluid stream integrating with the droplet to form a mixed droplet.

The droplets of the first sample fluid flow through a first channel separated from each other by immiscible carrier fluid and suspended in the immiscible carrier fluid. The droplets are delivered to the merge area, i.e., junction of the first channel with the second channel, by a pressure-driven flow generated by a positive displacement pump. While droplet arrives at the merge area, a bolus of a second sample fluid is protruding from an opening of the second channel into the first channel. Preferably, the channels are oriented perpendicular to each other. However, any angle that results in an intersection of the channels may be used.

The bolus of the second sample fluid stream continues to increase in size due to pumping action of a positive displacement pump connected to channel, which outputs a steady stream of the second sample fluid into the merge area. The flowing droplet containing the first sample fluid eventually contacts the bolus of the second sample fluid that is protruding into the first channel. Contact between the two sample fluids results in a portion of the second sample fluid being segmented from the second sample fluid stream and joining with the first sample fluid droplet to form a mixed droplet. In certain embodiments, each incoming droplet of first sample fluid is merged with the same amount of second sample fluid.

In certain embodiments, an electric charge is applied to the first and second sample fluids. Description of applying electric charge to sample fluids is provided in Link et al. (U.S. patent application number 2007/0003442) and European Patent Number EP2004316 to Raindance Technologies Inc, the content of each of which is incorporated by reference herein in its entirety. Electric charge may be created in the first and second sample fluids within the carrier fluid using any suitable technique, for example, by placing the first and second sample fluids within an electric field (which may be AC, DC, etc.), and/or causing a reaction to occur that causes the first and second sample fluids to have an electric charge, for example, a chemical reaction, an ionic reaction, a photocatalyzed reaction, etc.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof. In some cases, transparent or substantially transparent electrodes can be used.

The electric field facilitates rupture of the interface separating the second sample fluid and the droplet. Rupturing the interface facilitates merging of bolus of the second sample fluid and the first sample fluid droplet. The forming mixed droplet continues to increase in size until it a portion of the second sample fluid breaks free or segments from the second sample fluid stream prior to arrival and merging of the next droplet containing the first sample fluid. The segmenting of the portion of the second sample fluid from the second sample fluid stream occurs as soon as the shear force exerted on the forming mixed droplet by the immiscible carrier fluid overcomes the surface tension whose action is to keep the segmenting portion of the second sample fluid connected with the second sample fluid stream. The now fully formed mixed droplet continues to flow through the first channel.

In other embodiments, the rupture of the interface can be spontaneous, or the rupture can be facilitated by surface chemistry. The invention is not limited in regard to the method of rupture at the interface, as rupture can be brought about by any means.

In the context of PCR, in a preferred embodiment, the first sample fluid contains ssDNA templates. Droplets of the first sample fluid are formed as described above. Those droplets will include the ssDNA templates. In certain embodiments, some of the droplets will include only one single ssDNA template while other droplets contain no ssDNA template, and thus digital PCR can be conducted. In a preferred embodiment, the droplets are formed in the presence of reagents and enzymes needed for subsequent PCR reactions. In other embodiments, a second sample fluid contains reagents for the PCR reaction. Such reagents generally include Taq polymerase, deoxynucleotides of type A, C, G and T, magnesium chloride, and forward and (optionally) reverse primers, all suspended within an aqueous buffer. The second fluid also includes detectably labeled probes for detection of the amplified target nucleic acid, the details of which are discussed below. In an embodiment in which the PCR reagents are in a separate droplet, a droplet containing the nucleic acid is caused to merge with the PCR reagents in the second fluid as described above, producing a droplet that includes Taq polymerase, deoxynucleotides of type A, C, G and T, magnesium chloride, forward and reverse primers, detectably labeled probes, and the target nucleic acid. In another embodiment, the first fluid can contain the template DNA and PCR master mix (defined below), and the second fluid can contain the forward and reverse primers and the probe. The invention is not restricted in any way regarding the constituency of the first and second fluidics for PCR or digital PCR. For example, in some embodiments, the template DNA is contained in the second fluid inside droplets.

Target Amplification

Methods of the invention further involve amplifying the target nucleic acid in each droplet. Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification, transcription based amplification system, nucleic acid sequence-based amplification, rolling circle amplification, and hyper-branched rolling circle amplification.

In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence.

To effect amplification, primers are annealed to their complementary sequence within the target molecule. Following annealing, the primers are extended with a polymerase so as to form a new complementary strand. The steps of denaturation, primer annealing and polymerase extension can be repeated many times (i.e., denaturation, annealing and extension constitute one cycle; there can be numerous cycles) to obtain a high concentration of an amplified segment of a desired target sequence. The length of the amplified segment of the desired target sequence is determined by relative positions of the primers with respect to each other and by cycling parameters, and therefore, this length is a controllable parameter.

Methods for performing PCR in droplets are shown for example in Link et al. (U.S. patent application numbers 2008/0014589, 2008/0003142, and 2010/0137163), Anderson et al. (U.S. Pat. No. 7,041,481 and which reissued as RE41,780) and European publication number EP2047910 to Raindance Technologies Inc. The content of each of which is incorporated by reference herein in its entirety.

The sample droplet may be pre-mixed with a primer or primers, or the primer or primers may be added to the droplet. In some embodiments, droplets created by segmenting the starting sample are merged with a second set of droplets including one or more primers for the target nucleic acid in order to produce final droplets. The merging of droplets can be accomplished using, for example, one or more droplet merging techniques described for example in Link et al. (U.S. patent application numbers 2008/0014589, 2008/0003142, and 2010/0137163) and European publication number EP2047910 to Raindance Technologies Inc.

In embodiments involving merging of droplets, two droplet formation modules are used. In one embodiment, a first droplet formation module produces the sample droplets consistent with limiting or terminal dilution of target ssDNA. A second droplet formation or reinjection module inserts droplets that contain reagents for a PCR reaction. Such droplets generally include the "PCR master mix" (known to those in the art as a mixture containing at least Taq polymerase, deoxynucleotides of type A, C, G and T, and magnesium chloride) and forward and reverse primers (known to those in the art collectively as "primers"), all suspended within an aqueous buffer. The second droplet also includes detectably labeled probes for detection of the amplified target nucleic acid, the details of which are discussed below. Different arrangements of reagents between the two droplet types is envisioned. For example, in another embodiment, the template droplets also contain the PCR master mix, but the primers and probes remain in the second droplets. Any arrangement of reagents and template DNA can be used according to the invention.

Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. The simplest equation for determining the melting temperature of primers smaller than 25 base pairs is the Wallace Rule (Td=2(A+T)+4(G+C)). Another method for determining the melting temperature of primers is the nearest neighbor method Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The $T_M$ (melting or annealing temperature) of each primer is calculated using software programs such as Oligo Design, available from Invitrogen Corp.

In one embodiment, the droplet formation modules are arranged and controlled to produce an interdigitation of sample droplets and PCR reagent droplets flowing through a channel. Such an arrangement is described for example in Link et al. (U.S. patent application numbers 2008/0014589, 2008/0003142, and 2010/0137163) and European publication number EP2047910 to Raindance Technologies Inc.

A sample droplet is then caused to merge with a PCR reagent droplet, producing a droplet that includes the PCR master mix, primers, detectably labeled probes, and the target nucleic acid. Droplets may be merged for example by: producing dielectrophoretic forces on the droplets using electric field gradients and then controlling the forces to cause the droplets to merge; producing droplets of different sizes that thus travel at different velocities, which causes the droplets to merge; and producing droplets having different viscosities that thus travel at different velocities, which causes the droplets to merge with each other. Each of those techniques is further described in Link et al. (U.S. patent application numbers 2008/0014589, 2008/0003142, and 2010/0137163) and European publication number EP2047910 to Raindance Technologies Inc. Further description of producing and controlling dielectrophoretic forces on droplets to cause the droplets to merge is described in Link et al. (U.S. patent application number 2007/0003442) and European Patent Number EP2004316 to Raindance Technologies Inc.

In another embodiment, called simple droplet generation, a single droplet formation module, or a plurality of droplet formation modules are arranged to produce droplets from a mixture already containing the template DNA, the PCR master mix, primers, and detectably labeled probes. In yet another embodiment, called co-flow, upstream from a single droplet formation module two channels intersect allowing two flow streams to converge. One flow stream contains one set of reagents and the template DNA, and the other contains the remaining reagents. In the preferred embodiment for co-flow, the template DNA and the PCR master mix are in one flow stream, and the primers and probes are in the other. However, the invention is not limited in regard to the constituency of either flow stream. For example, in another embodiment, one flow stream contains just the template DNA, and the other contains the PCR master mix, the primers, and the probes. On convergence of the flow streams in a fluidic intersection, the flow streams may or may not mix before the droplet generation nozzle. In either embodiment, some amount of fluid from the first stream, and some amount of fluid from the second stream are encapsulated within a single droplet. Following encapsulation, complete mixing occurs.

Once final droplets have been produced by any of the droplet forming embodiments above, or by any other embodiments, the droplets are thermal cycled, resulting in amplification of the target nucleic acid in each droplet. In certain embodiments, the droplets are collected off-chip as an emulsion in a PCR thermal cycling tube and then thermally cycled in a conventional thermal cycler. Temperature profiles for thermal cycling can be adjusted and optimized as with any conventional DNA amplification by PCR.

In certain embodiments, the droplets are flowed through a channel in a serpentine path between heating and cooling lines to amplify the nucleic acid in the droplet. The width and depth of the channel may be adjusted to set the residence time at each temperature, which can be controlled to anywhere between less than a second and minutes.

In certain embodiments, the three temperature zones are used for the amplification reaction. The three temperature zones are controlled to result in denaturation of double stranded nucleic acid (high temperature zone), annealing of primers (low temperature zones), and amplification of single stranded nucleic acid to produce double stranded nucleic acids (intermediate temperature zones). The temperatures within these zones fall within ranges well known in the art for conducting PCR reactions. See for example, Sambrook et al. (Molecular Cloning, A Laboratory Manual, 3$^{rd}$ edition, Cold Spring Harbor Laboratory Press, Cold Spring Harbor, N.Y., 2001).

In certain embodiments, the three temperature zones are controlled to have temperatures as follows: 95° C. ($T_H$), 55° C. ($T_L$), 72° C. ($T_M$). The prepared sample droplets flow through the channel at a controlled rate. The sample droplets first pass the initial denaturation zone ($T_H$) before thermal cycling. The initial preheat is an extended zone to ensure that nucleic acids within the sample droplet have denatured successfully before thermal cycling. The requirement for a preheat zone and the length of denaturation time required is dependent on the chemistry being used in the reaction. The samples pass into the high temperature zone, of approximately 95° C., where the sample is first separated into single stranded DNA in a process called denaturation. The sample then flows to the low temperature, of approximately 55° C., where the hybridization process takes place, during which the primers anneal to the complementary sequences of the sample. Finally, as the sample flows through the third medium temperature, of approximately 72° C., the polymerase process occurs when the primers are extended along the single strand of DNA with a thermostable enzyme. Methods for controlling the temperature in each zone may include but are not limited to electrical resistance, Peltier junction, microwave radiation, and illumination with infrared radiation.

The nucleic acids undergo the same thermal cycling and chemical reaction as the droplets passes through each thermal cycle as they flow through the channel. The total number of cycles in the device is easily altered by an extension of thermal zones or by the creation of a continuous loop structure. The sample undergoes the same thermal cycling and chemical reaction as it passes through N amplification cycles of the complete thermal device.

In other embodiments, the temperature zones are controlled to achieve two individual temperature zones for a PCR reaction. In certain embodiments, the two temperature zones are controlled to have temperatures as follows: 95° C. ($T_H$) and 60° C. ($T_L$). The sample droplet optionally flows through an initial preheat zone before entering thermal cycling. The preheat zone may be important for some chemistry for activation and also to ensure that double stranded nucleic acid in the droplets are fully denatured before the thermal cycling reaction begins. In an exemplary embodiment, the preheat dwell length results in approximately 10 minutes preheat of the droplets at the higher temperature.

The sample droplet continues into the high temperature zone, of approximately 95° C., where the sample is first separated into single stranded DNA in a process called denaturation. The sample then flows through the device to the low temperature zone, of approximately 60° C., where the hybridization process takes place, during which the primers anneal to the complementary sequences of the sample. Finally the polymerase process occurs when the primers are extended along the single strand of DNA with a thermostable enzyme. The sample undergoes the same thermal cycling and chemical reaction as it passes through each thermal cycle of the complete device. The total number of cycles in the device is easily altered by an extension of block length and tubing.

In another embodiment the droplets are created and/or merged on chip followed by their storage either on the same chip or another chip or off chip in some type of storage vessel such as a PCR tube. The chip or storage vessel containing the droplets is then cycled in its entirety to achieve the desired PCR heating and cooling cycles.

In another embodiment the droplets are collected in a chamber where the density difference between the droplets and the surrounding oil allows for the oil to be rapidly exchanged without removing the droplets. The temperature of the droplets can then be rapidly changed by exchange of the oil in the vessel for oil of a different temperature. This technique is broadly useful with two and three step temperature cycling or any other sequence of temperatures.

The invention is not limited by the method used to thermocycle the droplets. Any method of thermocycling the droplets may be used.

Target Detection

After amplification, droplets are flowed to a detection module for detection of amplification products. For embodiments in which the droplets are thermally cycled off-chip, the droplets require re-injection into either a second fluidic circuit for read-out—that may or may not reside on the same chip as the fluidic circuit or circuits for droplet generation—or in certain embodiments the droplets may be reinjected for read-out back into the original fluidic circuit used for droplet generation. The droplets may be individually analyzed and detected using any methods known in the art, such as detecting the presence or amount of a reporter. Generally, the detection module is in communication with one or more detection apparatuses. The detection apparatuses can be optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at a sorting module. Further description of detection modules and methods of detecting amplification products in droplets are shown in Link et al. (U.S. patent application numbers 2008/0014589, 2008/0003142, and 2010/0137163) and European publication number EP2047910 to Raindance Technologies Inc.

In certain embodiments, amplified target are detected using detectably labeled probes. In particular embodiments, the detectably labeled probes are optically labeled probes, such as fluorescently labeled probes. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)amino-fluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. Preferred fluorescent labels are FAM and VIC™ (from Applied Biosystems). Labels other than fluorescent labels are contemplated by the invention, including other optically-detectable labels.

In certain aspects, the droplets of the invention contain a plurality of detectable probes that hybridize to amplicons produced in the droplets. Members of the plurality of probes can each include the same detectable label, or a different detectable label. The plurality of probes can also include one or more groups of probes at varying concentration. The groups of probes at varying concentrations can include the same detectable label which vary in intensity, due to varying probe concentrations.

In some embodiments, the droplets of the invention contain a plurality of barcodes that hybridize to amplicons produced in the droplets or are incorporated into the amplicons. The barcodes may be used in lieu of fluorescent probes, to detect the presence of a target sequence, or the barcodes can be used in addition to fluorescent probes, to track a multitude of sample sources. A detectable barcode-type label can be any barcode-type label known in the art including, for example, barcoded magnetic beads (e.g., from Applied Biocode, Inc., Santa Fe Springs, Calif.), and nucleic acid sequences. Nucleic acid barcode sequences typically include a set of oligonucleotides ranging from about 4 to about 20 oligonucleotide bases (e.g., 8-10 oligonucleotide bases) and uniquely encode a discrete library member without containing significant homology to any sequence in the targeted sample.

The barcode sequence generally includes features useful in sequencing reactions. For example, the barcode sequences are designed to have minimal or no homopolymer regions, i.e., 2 or more of the same base in a row such as AA or CCC, within the barcode sequence. The barcode sequences are also designed so that they are at least one edit distance away from the base addition order when performing base-by-base sequencing, ensuring that the first and last base do not match the expected bases of the sequence. In certain embodiments, the barcode sequences are designed to be correlated to a particular subject, allowing subject samples to be distinguished. Designing barcodes is shown U.S. Pat. No. 6,235,475, the contents of which are incorporated by reference herein in their entirety.

In some instances, the primers used in the invention may include barcodes such that the barcodes will be incorporated into the amplified products. For example, the unique barcode sequence could be incorporated into the 5' end of the primer, or the barcode sequence could be incorporated into the 3' end of the primer. In some embodiments, the barcodes may be incorporated into the amplified products after amplification. For example, a suitable restriction enzyme (or other endonuclease) may be introduced to a sample, e.g., a droplet, where it will cut off an end of an amplification product so that a barcode can be added with a ligase. Attaching barcode sequences to nucleic acids is shown in U.S. Pub. 2008/0081330 and PCT/US09/64001, the content of each of which is incorporated by reference herein in its entirety. Methods for designing sets of barcode sequences and other methods for attaching barcode sequences are shown in U.S. Pat. Nos. 6,138,077; 6,352,828; 5,636,400; 6,172,214; 6235,475; 7,393,665; 7,544,473; 5,846,719; 5,695,934; 5,604,097; 6,150,516; RE39,793; 7,537,897; 6,172,218; and 5,863,722, the content of each of which is incorporated by reference herein in its entirety.

In a separate embodiment the detection can occur by the scanning of droplets confined to a monolayer in a storage device that is transparent to the wavelengths or method or detection. Droplets stored in this fashion can be scanned either by the movement of the storage device by the scanner or the movement of the scanner over the storage device.

The invention is not limited to the TaqMan assay, as described above, but rather the invention encompasses the use of all fluorogenic DNA hybridization probes, such as molecular beacons, Solaris probes, scorpion probes, and any other probes that function by sequence specific recognition of target DNA by hybridization and result in increased fluorescence on amplification of the target sequence.

Digital PCR Performance in Droplets

Figure 3A:
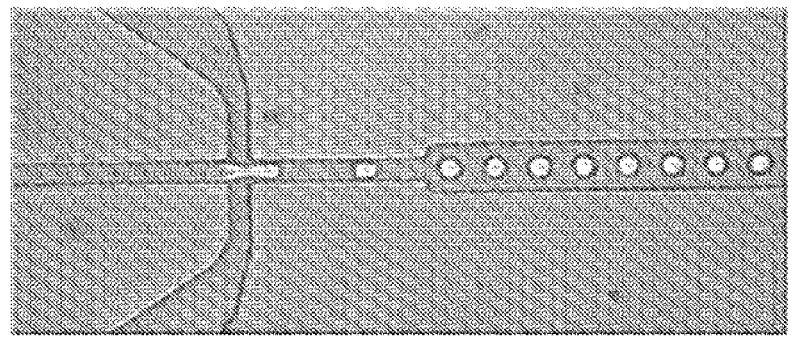
FIGS. 3A-3C depict an exemplary microfluidic system for droplet generation and readout.
Figure 3B:
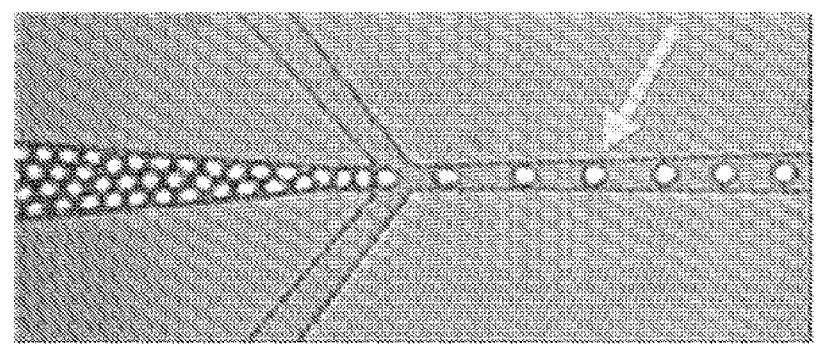
Figure 3C:
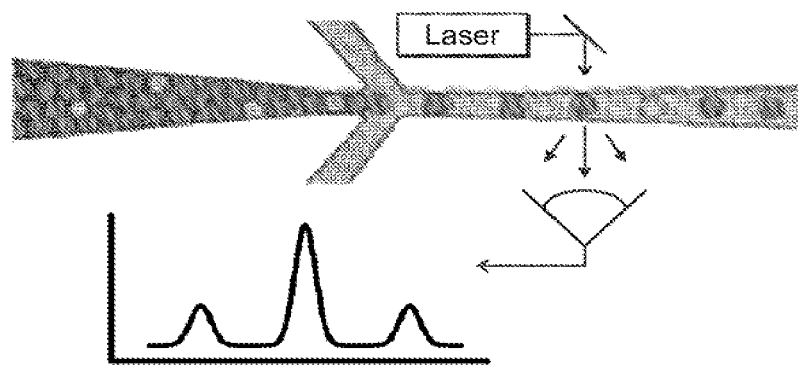

An exemplary microfluidic system for droplet generation and readout is depicted in FIGS. 3A-3C. The microfluidic system is capable of both droplet generation and readout. As shown in FIG. 3A (droplet generation chip), a continuous aqueous phase containing the PCR master mix, primers, and probes, and template DNA flows into the fluidic intersection from the left, and the carrier oil enters from the top and bottom. An emerging bolus of aqueous liquid is imaged inside the intersection just prior to snapping off into a discrete 4 pL droplet as the fluidic strain begins to exceed the surface tension of the aqueous liquid. The steady train of droplets leaving the intersection toward the right is collected off chip as a stable emulsion for thermal cycling. FIG. 3B depicts the droplet spacing for readout. Flows are arranged as in 3A, except instead of a continuous phase, the emulsion from (A) is injected from the left into the intersection after thermal cycling. The oil is drained from the emulsion during off-chip handling, hence the emulsion appears tightly packed in the image before the intersection. The oil introduced in the intersection separates the droplets and the fluorescence of each droplet is measured at the location marked by the arrow. FIG. 3C depicts a cartoon of droplet readout by fluorescence. The relatively infrequent PCR(+)

droplets (light gray) flow along with the majority of PCR(−) droplets (dark gray) toward the detector. The droplets are interrogated sequentially by laser induced fluorescence while passing through the detection region.

In a serial dilution, the average number of target DNA molecules per droplet—called the "occupancy" from this point forward—decreases in direct proportion to the DNA concentration. The occupancy is calculated from Poisson statistics using the following equation well known to those experienced in the art:

$$\text{occupancy} = \ln\left(\frac{P+N}{N}\right), \quad (1)$$

where P and N are the numbers of PCR(+) and PCR(−) droplets respectively.

Figure 4A:
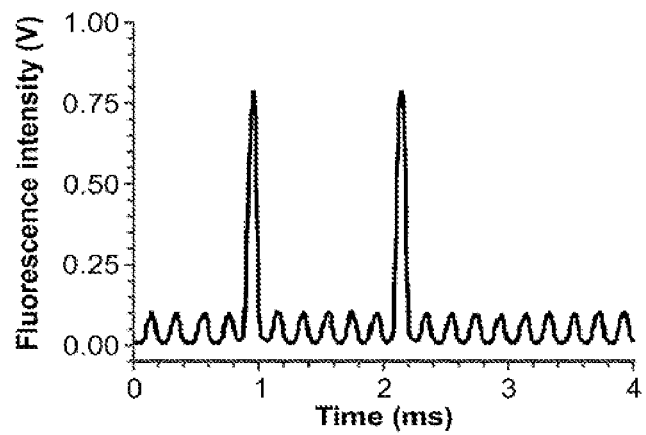
FIGS. 4A-4C depict the serial dilution of template DNA quantified by dPCR.
Figure 4B:
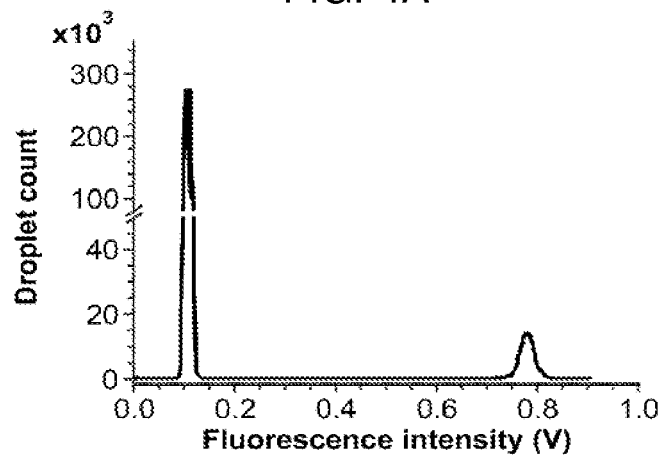
Figure 4C:
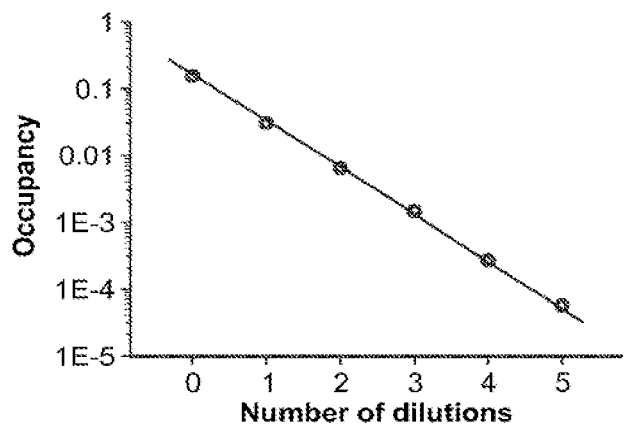

Droplets are analyzed by fluorescence while flowing through the readout chip to count the numbers of PCR(+) and PCR(−) droplets (see FIG. 3C). As each droplet passes the detection zone (marked with an arrow in FIG. 3B), a burst of fluorescence is observed. To account for small run-to-run differences in the fluorescence intensity that can occur due to different chip positioning, etc., each set of data is scaled such that the average fluorescence intensity of the empty droplets is 0.1 V. FIG. 4A shows a very short duration of a typical trace of fluorescence bursts from individual droplets for the sample with the highest DNA concentration in the series. PCR(+) and PCR(−) droplets are easily discriminated by fluorescence intensity. The two large bursts of fluorescence peaking at ~0.8 V arise from the PCR(+) droplets, whereas smaller bursts, due to incomplete fluorescence quenching in the PCR(−) droplets, peak at ~0.1 V. A histogram of peak intensities from the complete data set reveals two clear populations centered at 0.10 and 0.78 V (FIG. 4B), demonstrating that the trend evident in the short trace in FIG. 4A is stable over much longer periods of time. Integration over the two populations in FIG. 4B yields a total of 197,507 PCR(+) and 1,240,126 PCR(−) droplets. Hence the occupancy was 0.15 for this sample by Eqn. 1, corresponding to the expected occupancy of 0.18 based on the measured DNA concentration of 110 ng/μL. The occupancy is measured for each sample in the serial dilution and fit to the dilution equation:

$$\text{occupancy}(n) = \frac{A}{f^n}, \quad (2)$$

where n is the number of dilutions, A is the occupancy at the starting concentration (n=0), and f is the dilution factor. The linear fit was in excellent agreement with the data, with an $R^2$ value of 0.9999 and the fitted dilution factor of 4.8 in close agreement with the expected value of 5.0.

Copy Number Assay

Figure 5A:
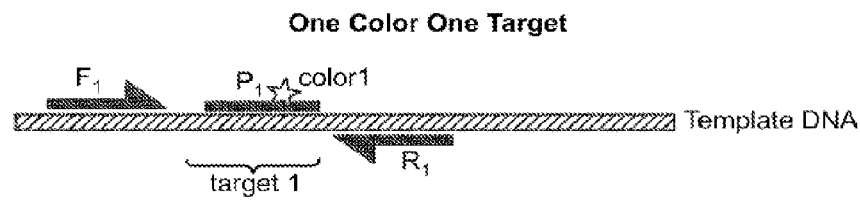
FIGS. 5A-5E are a series of schematic depicting one-color detection of a genetic sequence with a microfluidic device.
Figure 5B:
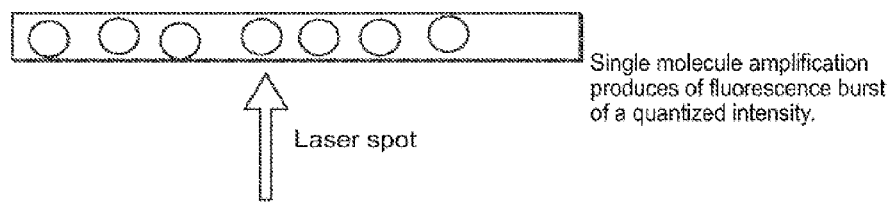
Figure 5C:
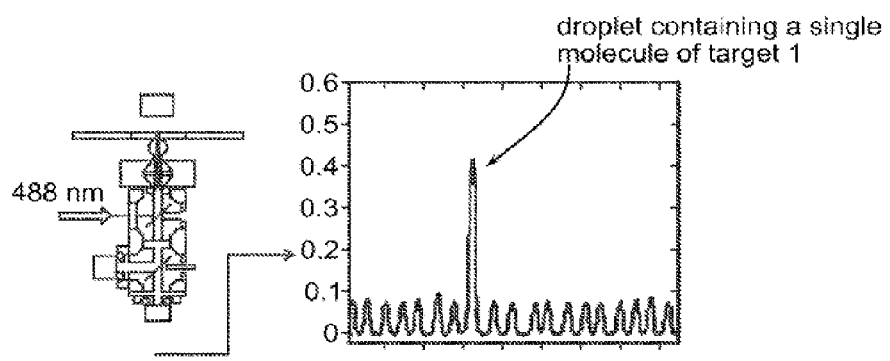
Figure 5D:
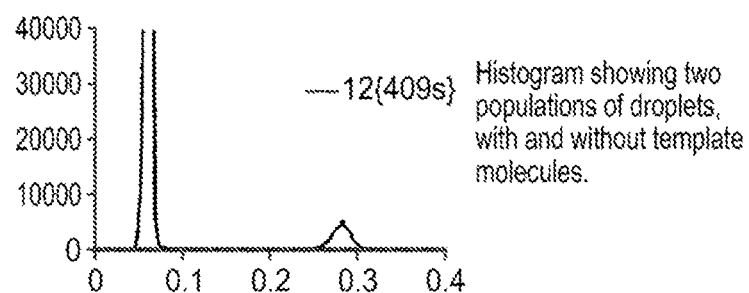
Figure 5E:
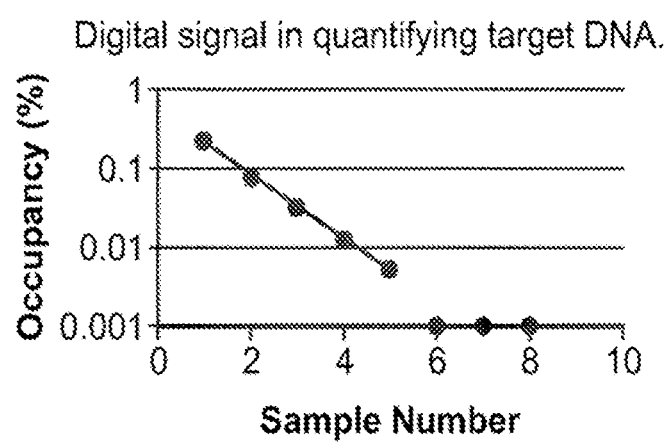

Traditional digital PCR methods involve the use of a single labeled probe specific for an individual target. FIGS. 5A-5E are schematics depicting one-color detection of a target dsDNA sequence using droplet based digital PCR. The method depicted in FIGS. 5A-5E is most useful for amplifying ssDNA that has been expanded to a dsDNA using, for example, a reverse transcriptase. As shown in FIG. 5A, a template DNA is amplified with a forward primer (F1) and a reverse primer (R1). Probe (P1) labeled with a fluorophore of color 1 binds to the target genetic sequence (target 1). Microdroplets are made of diluted solution of template DNA under conditions of limiting or terminal dilution. Droplets containing the target sequence emit fluorescence and are detected by laser (FIGS. 5B-5C). The number of microcapsules either containing or not containing the target sequence is shown in a histogram (FIG. 5D) and quantified (FIG. 5E). In embodiments where a ssDNA is initially amplified only the forward primer (F1) is needed, however the PCR master mix will always contain two primers because half of the ssDNA will bind with F1 and half of the ssDNA will bind with F2.

Data Analysis

One method of the invention involves histogram-based data presentation and analysis for identifying and characterizing populations of statistically similar droplets that arise from unique probe signatures (color and intensity), and for discriminating one population of droplets from the others. Another method of the invention involves histogram-based data presentation and analysis for identifying and selecting populations of droplets based on unique signatures from optical labels. Examples of one and two-dimensional histograms have been provided for these methods, but the invention is not limited in this regard. As described above, it is anticipated that greater numbers of colors will be used for both multiplexing and for optical labels. Hence, embodiments of the invention include histograms of dimensionality greater than two, such as 3, or 4, or up to 10, or up to 20. Histograms of dimensionality greater than 20 are also incorporated into the invention.

Another method of the invention involves the selection of droplets within histograms, either for counting, or for assay selection as in the use of optical labels, or for any other purpose. Methods of the invention include selections by boundaries, either closed or unclosed, of any possible shape and dimension. Methods of the invention also include selections of droplets that exhibit fluorescence from single types of fluorophores, or from multiple types of fluorophores, such as arising from multiple probes against a common DNA target.

In some embodiments, the analysis is based on counting, i.e., determining a number of droplets that contain only wild-type target, and determining a number of droplets that contain only a variant of the target. Such methods are well known in the art. See, e.g., Lapidus et al. (U.S. Pat. Nos. 5,670,325 and 5,928,870) and Shuber et al. (U.S. Pat. Nos. 6,203,993 and 6,214,558), the content of each of which is incorporated by reference herein in its entirety.

Generally, the presence of droplets containing only variant ssDNA is indicative of a disease, such as cancer. In certain embodiments, the variant is an allelic variant, such as an insertion, deletion, substitution, translocation, or single nucleotide polymorphism (SNP).

Biomarkers that are associated with cancer are known in the art. Biomarkers associated with development of breast cancer are shown in Erlander et al. (U.S. Pat. No. 7,504,214), Dai et al. (U.S. Pat. Nos. 7,514,209 and 7,171,311), Baker et al. (U.S. Pat. No. 7,056,674 and U.S. Pat. No. 7,081,340), Erlander et al. (US 2009/0092973). The contents of the patent application and each of these patents are incorporated by reference herein in their entirety. Biomarkers associated with development of cervical cancer are shown in Patel (U.S. Pat. No. 7,300,765), Pardee et al. (U.S. Pat. No. 7,153,700), Kim (U.S. Pat. No. 6,905,844), Roberts et al. (U.S. Pat. No. 6,316,208), Schlegel (US 2008/0113340), Kwok et al. (US 2008/0044828), Fisher et al. (US 2005/0260566), Sastry et al. (US 2005/0048467), Lai (US 2008/0311570) and Van Der Zee et al. (US 2009/0023137). Biomarkers associated with development of vaginal cancer are shown in Giordano (U.S. Pat. No. 5,840,506), Kruk (US 2008/0009005), Hellman et al. (Br J Cancer. 100(8):1303-1314, 2009). Biomarkers associated with development of brain cancers (e.g., glioma, cerebellum, medulloblastoma, astrocytoma, ependymoma, glioblastoma) are shown in D'Andrea (US 2009/0081237), Murphy et al. (US 2006/0269558), Gibson et al. (US 2006/0281089), and Zetter et al. (US 2006/0160762). Biomarkers associated with development of renal cancer are shown in Patel (U.S. Pat. No. 7,300,765), Soyupak et al. (U.S. Pat. No. 7,482,129), Sahin et al. (U.S. Pat. No. 7,527,933), Price et al. (U.S. Pat. No. 7,229,770), Raitano (U.S. Pat. No. 7,507,541), and Becker et al. (US 2007/0292869). Biomarkers associated with development of hepatic cancers (e.g., hepatocellular carcinoma) are shown in Home et al. (U.S. Pat. No. 6,974,667), Yuan et al. (U.S. Pat. No. 6,897,018), Hanausek-Walaszek et al. (U.S. Pat. No. 5,310,653), and Liew et al. (US 2005/0152908). Biomarkers associated with development of gastric, gastrointestinal, and/or esophageal cancers are shown in Chang et al. (U.S. Pat. No. 7,507,532), Bae et al. (U.S. Pat. No. 7,368,255), Muramatsu et al. (U.S. Pat. No. 7,090,983), Sahin et al. (U.S. Pat. No. 7,527,933), Chow et al. (US 2008/0138806), Waldman et al. (US 2005/0100895), Goldenring (US 2008/0057514), An et al. (US 2007/0259368), Guilford et al. (US 2007/0184439), Wirtz et al. (US 2004/0018525), Filella et al. (Acta Oncol. 33(7):747-751, 1994), Waldman et al. (U.S. Pat. No. 6,767,704), and Lipkin et al. (Cancer Research, 48:235-245, 1988). Biomarkers associated with development of ovarian cancer are shown in Podust et al. (U.S. Pat. No. 7,510,842), Wang (U.S. Pat. No. 7,348,142), O'Brien et al. (U.S. Pat. Nos. 7,291,462, 6,942,978, 6,316,213, 6,294,344, and 6,268,165), Ganetta (U.S. Pat. No. 7,078,180), Malinowski et al. (US 2009/0087849), Beyer et al. (US 2009/0081685), Fischer et al. (US 2009/0075307), Mansfield et al. (US 2009/0004687), Livingston et al. (US 2008/0286199), Farias-Eisner et al. (US 2008/0038754), Ahmed et al. (US 2007/0053896), Giordano (U.S. Pat. No. 5,840,506), and Tchagang et al. (Mol Cancer Ther, 7:27-37, 2008). Biomarkers associated with development of head-and-neck and thyroid cancers are shown in Sidransky et al. (U.S. Pat. No. 7,378,233), Skolnick et al. (U.S. Pat. No. 5,989,815), Budiman et al. (US 2009/0075265), Hasina et al. (Cancer Research, 63:555-559, 2003), Kebebew et al. (US 2008/0280302), and Ralhan (Mol Cell Proteomics, 7(6):1162-1173, 2008). The contents of each of the articles, patents, and patent applications are incorporated by reference herein in their entirety. Biomarkers associated with development of colorectal cancers are shown in Raitano et al. (U.S. Pat. No. 7,507,541), Reinhard et al. (U.S. Pat. No. 7,501,244), Waldman et al. (U.S. Pat. No. 7,479,376); Schleyer et al. (U.S. Pat. No. 7,198,899); Reed (U.S. Pat. No. 7,163,801), Robbins et al. (U.S. Pat. No. 7,022,472), Mack et al. (U.S. Pat. No. 6,682,890), Tabiti et al. (U.S. Pat. No. 5,888,746), Budiman et al. (US 2009/0098542), Karl (US 2009/0075311), Arjol et al. (US 2008/0286801), Lee et al. (US 2008/0206756), Mori et al. (US 2008/0081333), Wang et al. (US 2008/0058432), Belacel et al. (US 2008/0050723), Stedronsky et al. (US 2008/0020940), An et al. (US 2006/0234254), Eveleigh et al. (US 2004/0146921), and Yeatman et al. (US 2006/0195269). Biomarkers associated with development of prostate cancer are shown in Sidransky (U.S. Pat. No. 7,524,633), Platica (U.S. Pat. No. 7,510,707), Salceda et al. (U.S. Pat. No. 7,432,064 and U.S. Pat. No. 7,364,862), Siegler et al. (U.S. Pat. No. 7,361,474), Wang (U.S. Pat. No. 7,348,142), Ali et al. (U.S. Pat. No. 7,326,529), Price et al. (U.S. Pat. No. 7,229,770), O'Brien et al. (U.S. Pat. No. 7,291,462), Golub et al. (U.S. Pat. No. 6,949,342), Ogden et al. (U.S. Pat. No. 6,841,350), An et al. (U.S. Pat. No. 6,171,796), Bergan et al. (US 2009/0124569), Bhowmick (US 2009/0017463), Srivastava et al. (US 2008/0269157), Chinnaiyan et al. (US 2008/0222741), Thaxton et al. (US 2008/0181850), Dahary et al. (US 2008/0014590), Diamandis et al. (US 2006/0269971), Rubin et al. (US 2006/0234259), Einstein et al. (US 2006/0115821), Paris et al. (US 2006/0110759), Condon-Cardo (US 2004/0053247), and Ritchie et al. (US 2009/0127454). Biomarkers associated with development of pancreatic cancer are shown in Sahin et al. (U.S. Pat. No. 7,527,933), Rataino et al. (U.S. Pat. No. 7,507,541), Schleyer et al. (U.S. Pat. No. 7,476,506), Domon et al. (U.S. Pat. No. 7,473,531), McCaffey et al. (U.S. Pat. No. 7,358,231), Price et al. (U.S. Pat. No. 7,229,770), Chan et al. (US 2005/0095611), Mitchl et al. (US 2006/0258841), and Faca et al. (PLoS Med 5(6):e123, 2008). Biomarkers associated with development of lung cancer are shown in Sahin et al. (U.S. Pat. No. 7,527,933), Hutteman (U.S. Pat. No. 7,473,530), Bae et al. (U.S. Pat. No. 7,368,255), Wang (U.S. Pat. No. 7,348,142), Nacht et al. (U.S. Pat. No. 7,332,590), Gure et al. (U.S. Pat. No. 7,314,721), Patel (U.S. Pat. No. 7,300,765), Price et al. (U.S. Pat. No. 7,229,770), O'Brien et al. (U.S. Pat. No. 7,291,462 and U.S. Pat. No. 6,316,213), Muramatsu et al. (U.S. Pat. No. 7,090,983), Carson et al. (U.S. Pat. No. 6,576,420), Giordano (U.S. Pat. No. 5,840,506), Guo (US 2009/0062144), Tsao et al. (US 2008/0176236), Nakamura et al. (US 2008/0050378), Raponi et al. (US 2006/0252057), Yip et al. (US 2006/0223127), Pollock et al. (US 2006/0046257), Moon et al. (US 2003/0224509), and Budiman et al. (US 2009/0098543). Biomarkers associated with development of skin cancer (e.g., basal cell carcinoma, squamous cell carcinoma, and melanoma) are shown in Roberts et al. (U.S. Pat. No. 6,316,208), Polsky (U.S. Pat. No. 7,442,507), Price et al. (U.S. Pat. No. 7,229,770), Genetta (U.S. Pat. No. 7,078,180), Carson et al. (U.S. Pat. No. 6,576,420), Moses et al. (US 2008/0286811), Moses et al. (US 2008/0268473), Dooley et al. (US 2003/0232356), Chang et al. (US 2008/0274908), Alani et al. (US 2008/0118462), Wang (US 2007/0154889), and Zetter et al. (US 2008/0064047). Biomarkers associated with development of multiple myeloma are shown in Coignet (U.S. Pat. No. 7,449,303), Shaughnessy et al. (U.S. Pat. No. 7,308,364), Seshi (U.S. Pat. No. 7,049,072), and Shaughnessy et al. (US 2008/0293578, US 2008/0234139, and US 2008/0234138). Biomarkers associated with development of leukemia are shown in Ando et al. (U.S. Pat. No. 7,479,371), Coignet (U.S. Pat. No. 7,479,370 and U.S. Pat. No. 7,449,303), Davi et al. (U.S. Pat. No. 7,416,851), Chiorazzi (U.S. Pat. No. 7,316,906), Seshi (U.S. Pat. No. 7,049,072), Van Baren et al. (U.S. Pat. No. 6,130,052), Taniguchi (U.S. Pat. No. 5,643,729), Insel et al. (US 2009/0131353), and Van Bockstaele et al. (Blood Rev. 23(1):25-47, 2009). Biomarkers associated with development of lymphoma are shown in Ando et al. (U.S. Pat. No. 7,479,371), Levy et al. (U.S. Pat. No. 7,332,280), and Arnold (U.S. Pat. No. 5,858,655). Biomarkers associated with development of bladder cancer are shown in Price et al. (U.S. Pat. No. 7,229,770), Orntoft (U.S. Pat. No. 6,936,417), Haak-Frendscho et al. (U.S. Pat. No. 6,008,003), Feinstein et al. (U.S. Pat. No. 6,998,232), Elting et al. (US 2008/0311604), and Wewer et al. (2009/0029372). The content of each of the above references is incorporated by reference herein in its entirety. Devices and methods described herein may be used to assess the quality of a sample to be analyzed for methylation. DNA methylation is a chemical modification of DNA performed by enzymes called methyltransferases, in which a methyl group (m) is added to certain cytosines (C) of DNA, to yield 5-methylcytosine. This non-mutational (epigenetic) process (mC) is a critical factor in gene expression regulation. See, e.g., J. G. Herman, Seminars in Cancer Biology, 9: 359-67, 1999. Research suggests genes with high levels of 5-methylcytosine in a promoter region are transcriptionally silent, which allows unchecked cell proliferation. Additionally, it is likely that there a correlation between gene transcription and undermethylation. Methylation patterns of DNA from cancer cells are significantly different from those of normal cells. Therefore, detection of methylation patterns in appropriately selected genes of cancer cells can lead to discrimination of cancer cells from normal (i.e., non-cancerous) cells, thereby providing an approach to early detection of cancer.

In certain embodiments, methods of the invention may be used to monitor a patient for recurrence of a cancer. Since the patient has already been treated for the cancer, the genetic profile and particular mutation(s) associated with that patient's cancer are already known. Probes may be designed that specifically hybridize to the region of the nucleic acid that contains the mutation(s) that is indicative of the cancer for which the patient was previously treated. A patient's sample (e.g., pus, sputum, semen, urine, blood, saliva, stool, or cerebrospinal fluid) may then be analyzed as described above to determine whether the mutant allele(s) is detected in the sample, the presence of which being indicative of recurrence of the cancer.

Release of Target from Droplet

Methods of the invention may further involve releasing amplified target molecules from the droplets for further analysis. Methods of releasing amplified target molecules from the droplets are shown in for example in Link et al. (U.S. patent application numbers 2008/0014589, 2008/0003142, and 2010/0137163) and European publication number EP2047910 to RainDance Technologies Inc.

In certain embodiments, sample droplets are allowed to cream to the top of the carrier fluid. By way of non-limiting example, the carrier fluid can include a perfluorocarbon oil that can have one or more stabilizing surfactants. The droplet rises to the top or separates from the carrier fluid by virtue of the density of the carrier fluid being greater than that of the aqueous phase that makes up the droplet. For example, the perfluorocarbon oil used in one embodiment of the methods of the invention is 1.8, compared to the density of the aqueous phase of the droplet, which is 1.0.

The creamed liquids are then placed onto a second carrier fluid which contains a de-stabilizing surfactant, such as a perfluorinated alcohol (e.g. 1H,1H,2H,2H-Perfluoro-1-octanol). The second carrier fluid can also be a perfluorocarbon oil. Upon mixing, the aqueous droplets begins to coalesce, and coalescence is completed by brief centrifugation at low speed (e.g., 1 minute at 2000 rpm in a microcentrifuge). The coalesced aqueous phase can now be removed and the further analyzed.

The released amplified material can also be subjected to further amplification by the use tailed primers and secondary PCR primers. In this embodiment the primers in the droplet contain an additional sequence or tail added onto the 5' end of the sequence specific portion of the primer. The sequences for the tailed regions are the same for each primer pair and are incorporated onto the 5' portion of the amplicons during PCR cycling. Once the amplicons are removed from the droplets, another set of PCR primers that can hybridize to the tail regions of the amplicons can be used to amplify the products through additional rounds of PCR. The secondary primers can exactly match the tailed region in length and sequence or can themselves contain additional sequence at the 5' ends of the tail portion of the primer. During the secondary PCR cycling these additional regions also become incorporated into the amplicons. These additional sequences can include, but are not limited to adaptor regions utilized by sequencing platforms for library preparation and sequencing, sequences used as a barcoding function for the identification of samples multiplexed into the same reaction molecules for the separation of amplicons from the rest of the reaction materials such as biotin, digoxin, peptides, or antibodies and molecules such as fluorescent markers that can be used to identify the fragments.

In certain embodiments, the amplified target molecules are sequenced. In a particular embodiment, the sequencing is single-molecule sequencing-by-synthesis. Single-molecule sequencing is shown for example in Lapidus et al. (U.S. Pat. No. 7,169,560), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety.

Briefly, a single-stranded nucleic acid (e.g., DNA or cDNA) is hybridized to oligonucleotides attached to a surface of a flow cell. The single-stranded nucleic acids may be captured by methods known in the art, such as those shown in Lapidus (U.S. Pat. No. 7,666,593). The oligonucleotides may be covalently attached to the surface or various attachments other than covalent linking as known to those of ordinary skill in the art may be employed. Moreover, the attachment may be indirect, e.g., via the polymerases of the invention directly or indirectly attached to the surface. The surface may be planar or otherwise, and/or may be porous or non-porous, or any other type of surface known to those of ordinary skill to be suitable for attachment. The nucleic acid is then sequenced by imaging the polymerase-mediated addition of fluorescently-labeled nucleotides incorporated into the growing strand surface oligonucleotide, at single molecule resolution.

Determining the Nucleic Acid Make-Up of a Sample

Further aspects of the invention include methods for determining the nucleic acid make-up of a sample. Specifically, the method can determine the presence of a contiguous, intact nucleic acid, i.e., an unbroken chain of nucleotides, between two locations on the nucleic acid. Presence of a contiguous nucleic acid is determined via detection of both a first and second detectably labeled probe that hybridizes to a first and second location on the nucleic acid (e.g., a sequence, an oligomer, a polymer, a template, dsDNA). The detection of only one probe indicates a fragmented nucleic acid, in other words, a nucleic acid that is not contiguous through the entirety of the two aforementioned locations on the nucleic acid. In some embodiments, the method involves partitioning a sample comprising nucleic acid of different lengths into a plurality of partitioned portions, wherein each portion comprises, on average, a single nucleic acid molecule, introducing first and second primer pairs and first and second detectably labeled probes to the partitioned portions, wherein the first and second primer pairs are specific for first and second locations on the nucleic acid, the first and second locations being spaced apart from each other, and wherein the first probe hybridizes to the first location and the second probe hybridizes to the second location, amplifying the nucleic acid in the partitioned portions, the presence of signal from both probes indicating the presence of a nucleic acid that is contiguous between the first and second locations, and determining a nucleic acid make-up of the sample based upon results of the detecting step.

Specific methods for the partitioning, introducing, amplifying, and detecting steps have been presented throughout the present disclosure. Further detail on determination step is now presented. As mentioned above, determination of contiguous or intact nucleic acid involves detecting a first and second detectably labeled probe that hybridizes to a first and second location on a nucleic acid. The detection of only one probe indicates the presence of a fragment of the longer nucleic acid. In some embodiments, the determining step may involve comparing relative amounts of contiguous nucleic acid to relative amounts of non-contiguous nucleic acid. In other embodiments, the determining step involves comparing amount of contiguous nucleic acid or non-contiguous nucleic acid to a total amount of amino acid.

For sequencing and other extensive molecular biology studies, a sample comprising mostly intact nucleic acid is desirable and is conducive to accurate results. The presence of a relatively large population of nucleic acid fragments, i.e., non-contiguous nucleic acids, may indicate that a sample is not suitable for sequencing. Because sequencing is relatively expensive, knowing the make-up of the sample prior to testing is advantageous. This is especially so when the sample is an FFPE sample or some other form of preserved sample in which the nucleic acid of interest has degraded into fragments. In some embodiments, if less than 90% of the nucleic acid sample, e.g., less than 80% of the nucleic acid sample, e.g., less than 70% of the nucleic acid sample, e.g., less than 50% of the nucleic acid sample, e.g., less than 40% of the nucleic acid sample, e.g., less than 30% of the nucleic acid sample, e.g., less than 20% of the nucleic acid sample, e.g., less than 10% of the nucleic acid sample is fragmented, the nucleic acid sample is suitable for further sequencing. Accordingly, once the nucleic acid make-up of a sample is determined, a further step may involve sequencing the sample, enriching the sample, or sequencing the sample after enrichment. Furthermore, because the method of determining the nucleic acid make-up incorporates the dPCR methods described throughout the present disclosure, extremely small amounts of sample can be tested successfully. In some embodiments, the test sample may contain 50 ng or less of DNA or RNA.

The methods described herein are not limited to the use of two probes, however. In some embodiments a plurality of probes are used to give additional information about the properties of nucleic acids in a sample. For example, three probes could be used wherein one probe was one color (e.g., VIC™), and two probes were another color (e.g., FAM). Differences in intensity or polarization make it possible to distinguish between the probes of the same color, as discussed previously. Analysis using such a method may make it possible to determine the presence of multiple different contiguous lengths of nucleic acid molecules.

While methods described herein can encompass the use of several primer pairs, methods in accordance with the invention also encompass the use of a single primer or a single primer pair. In some embodiments, the method includes providing a fluid comprising the sample nucleic acid and a plurality of one or more primer pairs, wherein each primer pair has at least one unique related probe and is selected to be complementary to one or more sequences of known length. The method also includes partitioning the fluid into a plurality of partitions, wherein at least a first portion of the partitions comprise one molecule of the nucleic acid sample having sequences complementary to one or more of the primer pairs, and at least one related probe, and a second portion of the partitions comprise no molecules of the sample nucleic acid having sequences complementary to one or more of the primer pairs. The method further includes conducting a PCR reaction in the partitions, thereby changing a fluorescent property of the first portion of the partitions, detecting the fluorescent property of each partition, and determining the number of occurrences in the sample nucleic acid of one or more sequences of known length based on the detecting step. In some aspects of the invention, the method further includes comparing a first number of occurrences of a first sequence of known length to a second number of occurrences of a second sequence of a second known length.

Additional embodiments of the invention may also contemplate the use of a single primer or a single primer pair as well as rely on something other than a probe for detecting the amplified sequence. In certain embodiments, the method comprises partitioning a sample comprising nucleic acid of different lengths into a plurality of partitioned portions, wherein each portion comprises, on average a single nucleic acid molecule. The method further includes introducing at least one primer pair, in which each primer of the pair is specific for a first and second location on the nucleic acid, the first and second locations being spaced apart from each other. The method further includes amplifying the nucleic acid in the partitioned portions, detecting the amplicons in the partitioned portions, and determining a nucleic acid make-up of the sample based on the results of the detecting step. In certain embodiments, the amplicons may be detected with a probe, for example, a fluorescently labeled probe. In other embodiments, the amplicon may be detected with a dye that intercalates within the nucleic acid. The invention also contemplates any other means of detecting nucleic acid sequences known in the art that do not interfere with the other steps described herein.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

The invention claimed is:

1. A method for determining an amount of DNA in a sample, the method comprising:
   dissociating a plurality of double-stranded DNAs from a sample into a plurality of first strands and a plurality of second strands;
   partitioning the plurality of first strands and the plurality of second strands into a plurality of partitioned portions, at least some of the partitioned portions having only a first strand or only a second strand;
   detecting a presence or absence of a first strand or a second strand in a plurality of partitioned portions; and
   comparing the presence of a first strand or a second strand in a plurality of partitioned portions to the absence of a first strand or a second strand in a plurality of partitioned portions to determine an amount of DNA present in a sample.

2. The method of claim 1, wherein detecting comprises conducting a PCR reaction in at least some of the droplets, thereby changing a fluorescent property of at least some of the droplets, and assessing the fluorescent property of at least some of the droplets.

3. The method of claim 2, wherein conducting a PCR reaction comprises annealing a first strand or a second strand with a primer.

4. The method of claim 3, wherein the primer anneals with a human sequence mutation.

5. The method of claim 3, wherein the primer anneals with a pathogenic sequence.

6. The method of claim 3, wherein the primer anneals with a genetic marker for a disease.

7. The method of claim 1, wherein dissociating comprises heating the plurality of double-stranded DNAs.

8. The method of claim 7, wherein heating comprises raising the temperature of the plurality of double-stranded DNAs to at least 90° C.

9. The method of claim 7, further comprising cooling the plurality of first strands and the plurality of second strands after heating the plurality of double-stranded DNAs.

10. The method of claim 9, wherein cooling comprises reducing the temperature of the first or second strand to less than 20° C. in less than 60 seconds.

11. The method of claim 1, wherein the different partitioned portions comprise different droplets.

\* \* \* \* \*